United States Patent
Friesz et al.

(10) Patent No.: US 9,024,046 B2
(45) Date of Patent: May 5, 2015

(54) REDUCTIVE AMINATION PROCESS FOR PREPARATION OF DRONEDARONE USING AMINE INTERMEDIARY COMPOUND

(75) Inventors: Antal Friesz, Budapest (HU); Csaba Huszar, Budapest (HU)

(73) Assignee: Sanofi, Paris (FR)

(*) Notice: Subject to any disclaimer, the term of this patent is extended or adjusted under 35 U.S.C. 154(b) by 0 days.

(21) Appl. No.: 14/007,170

(22) PCT Filed: Mar. 27, 2012

(86) PCT No.: PCT/HU2012/000021
§ 371 (c)(1),
(2), (4) Date: Sep. 24, 2013

(87) PCT Pub. No.: WO2012/131410
PCT Pub. Date: Oct. 4, 2012

(65) Prior Publication Data
US 2014/0018554 A1    Jan. 16, 2014

(30) Foreign Application Priority Data
Mar. 29, 2011 (HU) ..................... 1100166

(51) Int. Cl.
C07D 307/00 (2006.01)
C07D 307/81 (2006.01)
C07D 307/85 (2006.01)
C07D 307/83 (2006.01)

(52) U.S. Cl.
CPC ............ C07D 307/81 (2013.01); C07D 307/85 (2013.01); C07D 307/83 (2013.01)

(58) Field of Classification Search
CPC ............................ C07D 307/83; C07D 307/85
USPC .................................................. 549/466, 468
See application file for complete search history.

(56) References Cited

U.S. PATENT DOCUMENTS

| 5,223,510 A | 6/1993 | Gubin et al. |
| 2004/0010032 A1 | 1/2004 | Biard |

FOREIGN PATENT DOCUMENTS

| EP | 0 471 609 A1 | 2/1992 |
| WO | WO 02/48078 A1 | 6/2002 |
| WO | WO 02/48132 A1 | 6/2002 |
| WO | WO 03/040120 A1 | 5/2003 |
| WO | WO 2010/116140 A1 | 10/2010 |

OTHER PUBLICATIONS

Database PubChem Compound, CID 10095002—Compound Summary: N-[3-[4-(3-aminopropoxy)benzoyl]-2-butyl-1-benzofuran-5-yl, Database accession No. 15082344, (Oct. 25, 2006).
International Search Report dated Jun. 12, 2012 issued in PCT/HU2012/000021.

*Primary Examiner* — Andrew D Kosar
*Assistant Examiner* — Raymond Covington
(74) *Attorney, Agent, or Firm* — Morrison & Foerster LLP

(57) ABSTRACT

The invention relates to a novel process for preparation of drohedarone of formula (I) and pharmaceutically acceptable salts thereof characterized in that a compound of formula (II) is reacted in the presence of a reductive agent with butyraldehyde and/or butanoic acid, and isolating the obtained product and, if desired, converting it into a pharmaceutically acceptable salt thereof. The invention also relates to some hovel intermediary compounds and the preparation thereof.

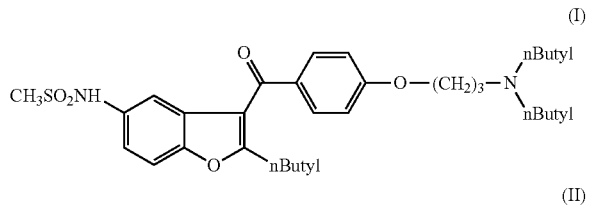

(I)

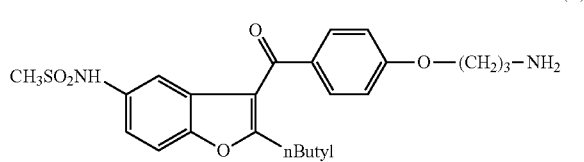

(II)

13 Claims, No Drawings

REDUCTIVE AMINATION PROCESS FOR PREPARATION OF DRONEDARONE USING AMINE INTERMEDIARY COMPOUND

FIELD OF THE INVENTION

This invention relates to a novel process for the preparation of dronedarone and pharmaceutically acceptable salts thereof, to novel intermediary compounds used in this process and their preparation.

TECHNICAL BACKGROUND

Dronedarone is a known drug for the treatment of arrhythmia and has the chemical name of N-[2-n-butyl-3-[4-[3-(di-n-butylamino)propoxy]benzoyl]benzofuran-5-yl]methanesulfonamide [see also formula (I) below]. There are some known processes for the preparation of dronedarone as follows:

In EP 0471609 the following scheme is disclosed for the preparation of dronedarone
[Process A]

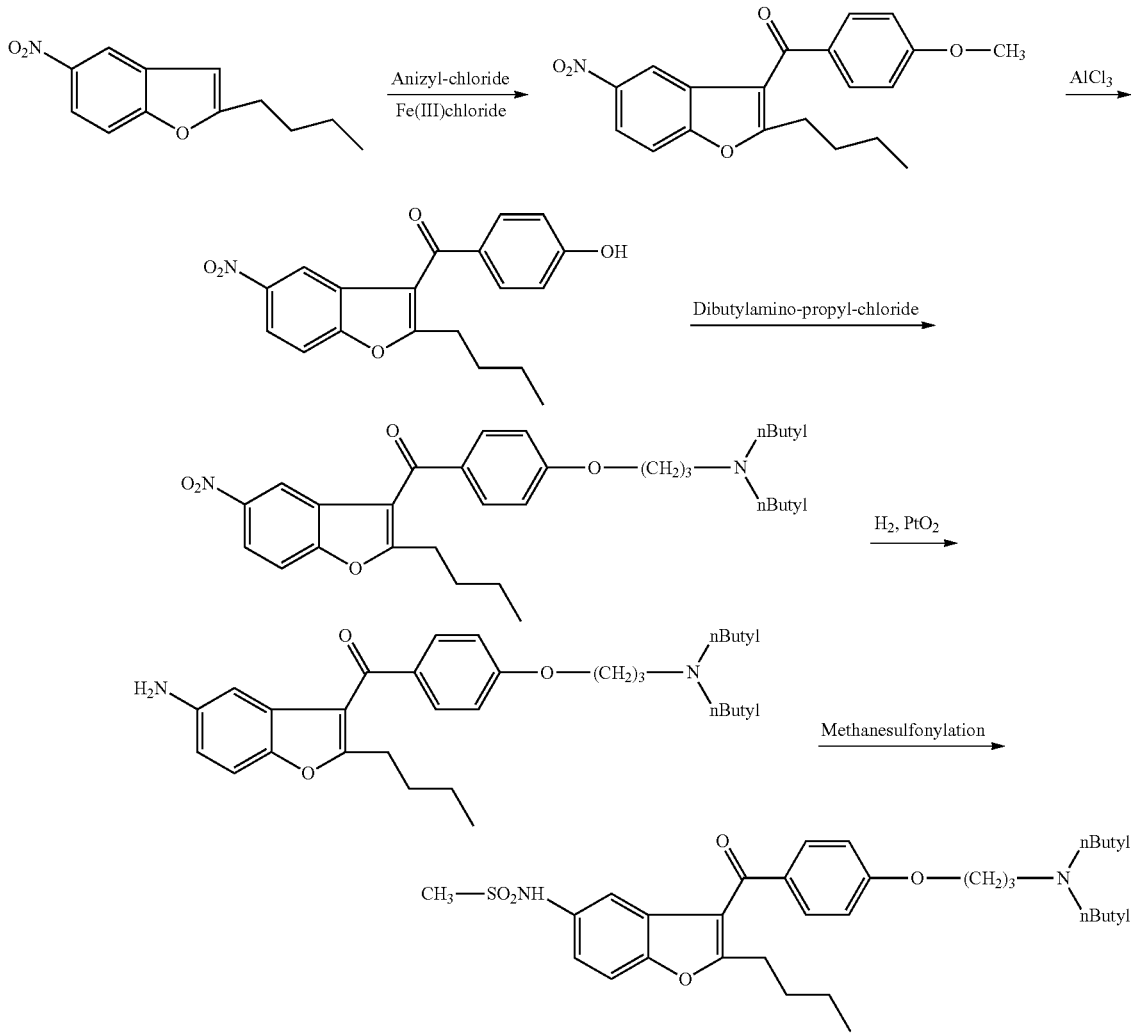

The above mentioned patent description discloses some new intermediary compounds, too.

In WO 02/48078 the following scheme is disclosed for the preparation of dronedarone
[Process B]:

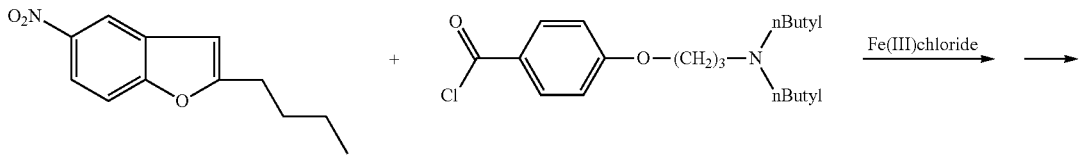

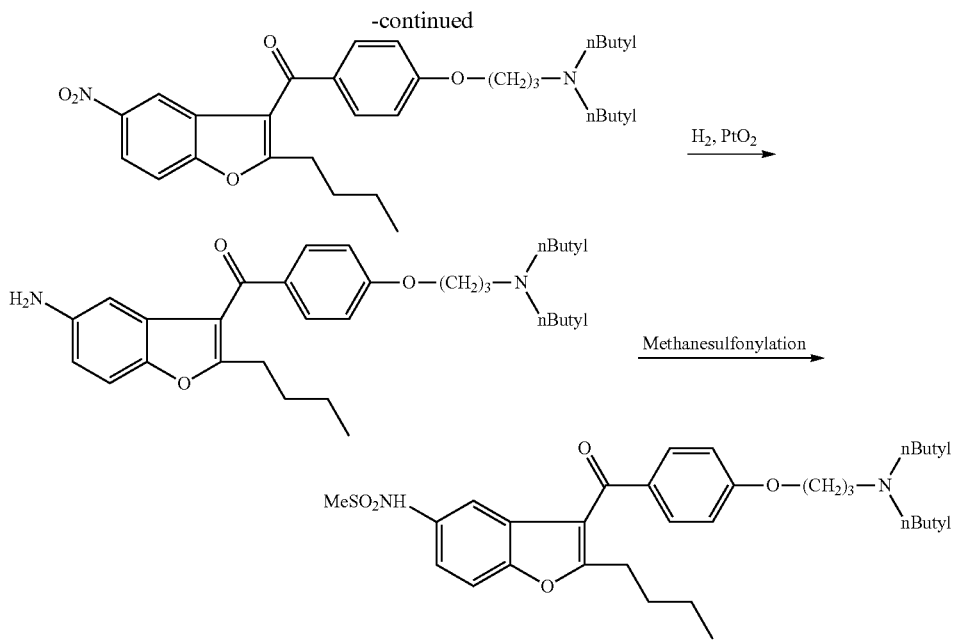

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so called superconvergent route. In the first step of it 5-amino-2-butyl-benzofuran

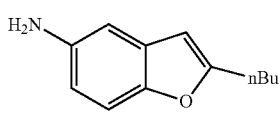

is mesylated and the obtained 2-butyl-5-methanesulfonamido-benzofuran (in HCl salt form) is further reacted in the next step as follows:

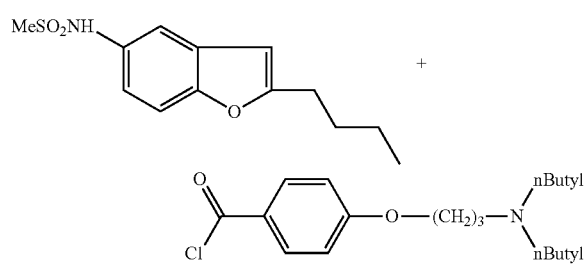

In this process the order of reaction steps are altered, the reduction and the methansulfonylation steps are performed at the beginning of the procedure. Besides the reaction route for preparation of dronedarone, the starting material 2-butyl-5-methansulfonamido-benzofuran and its preparation is also claimed.

From among the mentioned procedures the first one [Process A] is the so called linear synthesis. In this way of procedure the different parts of the dronedarone are stepwise built up on the starting compound. This method is the least economical because the step by step building of the chemical groups is performed where more and more complicated and expensive molecules are applied which rises the costs of preparation. Furthermore, it comprises complicated and dangerous reaction step because aluminium chloride is used in the cleaving reaction of the methoxy group which makes the industrial feasibility more complicated.

In WO 02/48078 (Process B) a shorter synthetic route is disclosed which makes this process more economical, but its last reaction step remained the methansulfonylation reaction of the amino group. This reaction step (see the method described in example 6 of WO 02/48078) is complicated and give a low yield, only 61.6%. Pure product can be obtained after purification using chromatographic column purification, which method is necessary because of the separation difficulties of the bis-methanesulfonylated product.

The process disclosed in WO 02/48132 (process C) is simpler and more economical taken into consideration the number of the reaction steps. Unfortunately, in the last reaction step rather impure dronedarone.HCl (hydrochloride salt) is formed which is the obvious consequence of the presence of dibutylamino group in the Friedel-Crafts reaction. According to Examples 3 and 4, the crude dronedarone hydrochloride salt is prepared with a yield of 90% which was further purified and finally the crude dronedarone base was produced with a yield of 86%. This base is reacted with hydrogen chloride gas dissolved in isopropanol which results in pure dronedarone hydrochloride salt. No yield was given for this reaction step. According to example 5 crude dronedarone hydrochloride salt was prepared with a yield of 90%, which was washed with water and reacted with hydrogen chloride gas dissolved in isopropanol, resulting dronedarone hydrochloride salt again. The quality of this product is not known. However, neither the components used in the Friedel-Crafts reaction nor the resulted products and by-products are soluble in water, the washing step with water cannot result any purification apart from the removal of inorganic salts.

SUMMARY OF THE INVENTION

The main aspect of the invention is a process for the preparation of dronedarone of formula (I) and pharmaceutically acceptable salts thereof,

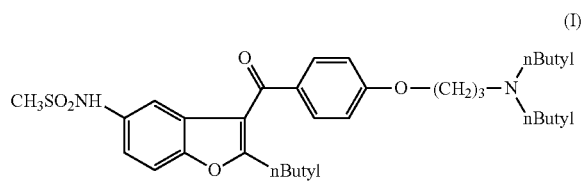

(I)

wherein a compound formula (II)

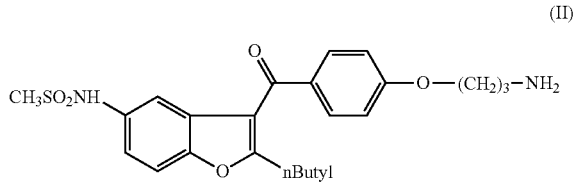

(II)

is reacted in the presence of a reductive agent with
a) butyraldehyde of formula (III) and/or

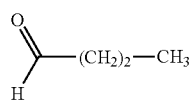

(III)

b) butanoic acid.

It was an aim during the elaboration of the present invention to provide a novel process for the preparation of dronedarone of formula (I) starting from known and commercially available materials and using simple and environmentally compatible reagents and solvents to afford high overall yields and good purity of the product. The present invention avoids the drawbacks of the procedures mentioned before, because the formation of dronedarone in the final step is completed with butyraldehyde and/or butanoic acid among reductive conditions, e.g. applying triacetoxyborohydride or sodium borohydride, respectively, as reductive agent.

We have found surprisingly that compound of formula (III) can be connected to the amino group in that way that after the reduction of the enamine formed a second aldehyde can be connected and reduced to tertiary amine at the same time.

Alternatively, the butylation procedure can be performed only using butanoic acid among reductive conditions, typically in the presence of sodium borohydride. The reaction can be performed in way where compound of formula (III) and butanoic acid are applied together as reagent.

It is also surprising that in the above reactions the di-n-butylation of the amino group (see the "right" side of the molecule) can be carried out without derivatizing the sulphonamide group taking place in the molecule, too (see the "left side" of the molecule).

The starting materials are commercially available; compound of formula (III) and the known reductive agents (e.g. triacetoxiborohydride and sodium borohydride) can be purchased.

Further aspects of the invention are the novel intermediary compounds and the methods for the preparation thereof (see, below in the "Detailed description of the invention" part).

DETAILED DESCRIPTION OF THE INVENTION

Therefore the present invention relates to a process for the preparation of dronedarone and pharmaceutically acceptable salts thereof. The whole process—starting from compounds available commercial sources—reads as follows:

A) For the preparation of a compound of formula (XIV)

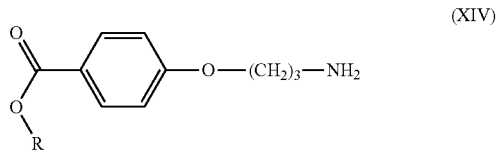

(XIV)

where R is alkyl,
a compound of formula (XV)

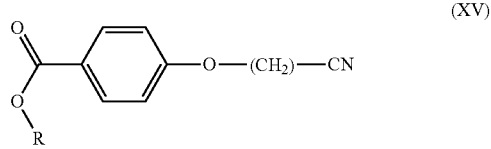

(XV)

where R is alkyl, is hydrogenated.

The reaction is carried out among usual hydrogenation conditions. For example, the hydrogenation process is carried out in a solvent in the presence of catalyst, e.g. Ni catalyst, typically Raney-Ni. Typically the solvent is selected from the group of $C_{1-4}$ alcohols, ethyl acetate and cyclohexane, typically the solvent is methanol or ethanol.

B) For the preparation of compound of formula (XIII)

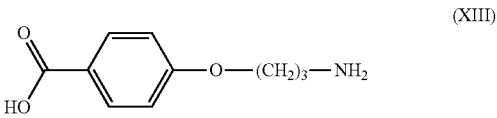

(XIII)

an above compound of formula (XIV) is hydrolyzed.

The hydrolyzation is carried out among known conditions, i.e. in an aqueous solvent with acids or bases under known reaction conditions. Typically the solvent is selected from the group of $C_{1-4}$ alcohols and ketones, typically the solvent is methanol or ethanol.

Typically the base is selected from the group of alkali hydroxides, e.g. it is sodium hydroxide or potassium hydroxide.

Typically the acid is selected from the group of inorganic strong acids, e.g it is hydrogen chloride.

C) For the preparation of compound of formula (XII)

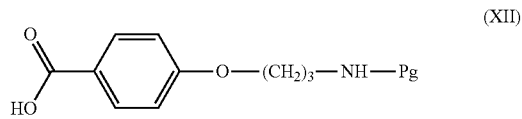

(XII)

where Pg is an amino protecting group, typically an A-CO— group, where A is alkyl, alkoxy, aryl or aryloxy group, e.g. it is ethoxycarbonyl, the above compound of formula (XIII) is reacted with a carboxylic acyl halogenide among alkaline conditions, i.e. in the presence of one or more base(s).

The above protection of compound of formula (XIII) can be carried out in a solvent, with a carboxylic acyl halogenide (typically with ethoxycarbonyl chloride) under known reaction conditions. Typically the solvent is selected from the group of water, ethyl acetate and ketones, typically the solvent is water.

Typically the base is selected from the group of alkali hydroxides, e.g. it is sodium hydroxide or potassium hydroxide.

D) For the preparation of a compound of formula (XI)

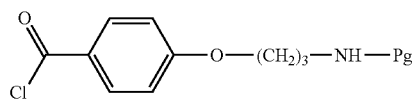

(XI)

where Pg is an amino protecting group, typically an A-CO— group, where A is alkyl, alkoxy, aryl or aryloxy group, e.g. it is ethoxycarbonyl, an above compound of formula (XII) is reacted with thionyl chloride in an inert solvent, typically between 15 to 40° C.

Typically the inert solvent is selected from the group of halogenated hydrocarbons, e.g. $CH_2Cl_2$.

E) For the preparation of compounds of formula (V)

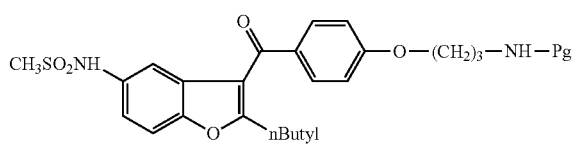

(V)

the compound of formula (X)

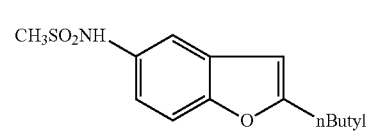

(X)

is reacted with an above, compound of formula (XI)

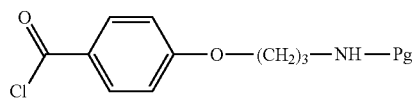

(XI)

under Friedel-Crafts reaction conditions, where Pg is amino protecting group, typically an A-CO— group, where A is alkyl, alkoxy, aryl or aryloxy group, e.g. it is ethoxycarbonyl.

The reaction is carried out halogenated or nitro group containing solvents, e.g. dichloromethane, dichloroethane, chlorobenzene, nitromethane, nitrobenzene. Catalyst also can be applied, e.g. $AlCl_3$, $FeCl_3$, $SnCl_4$, $TiCl_4$.

Compound (II) can be prepared from this compound (V) by removing Pg (see below).

Another way for the preparation of compound (II) reads as follows:

F) For the preparation of compound of formula (VII)

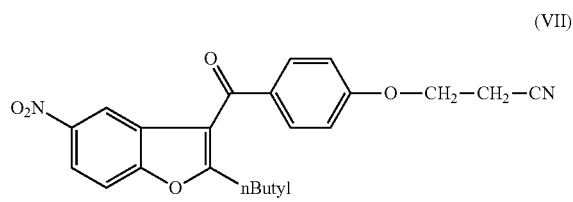

(VII)

the compound of formula (VIII)

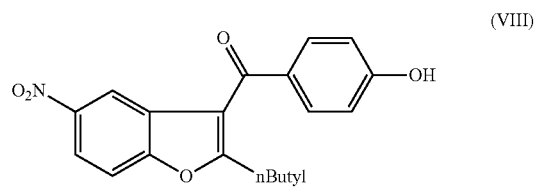

(VIII)

is reacted with acrylonitrile of formula $CH_2=CH—CN$ (IX).

Compound (VIII) is known from: EP 0 471 609 (Sanofi).

Typically the reaction is carried out in a solvent (which can be e.g. a $C_{1-4}$ alcohol, typically methanol or ethanol), and typically a strong basic catalyst is applied. This catalyst is selected typically from the group of alkali alkoxydes and quaternary ammonium hydroxides, and it can be e.g. benzyl-trimethylammonium hydroxide.

Typically the reaction is carried out in the excess of acrylonitrile as solvent at the boiling point of the solvent, e.g. about 70 to 90° C. Typically strong water free ammonium quaternary hydroxides or alkali alkoxydes can be applied as catalyst.

G) For the preparation of compound of formula (VI)

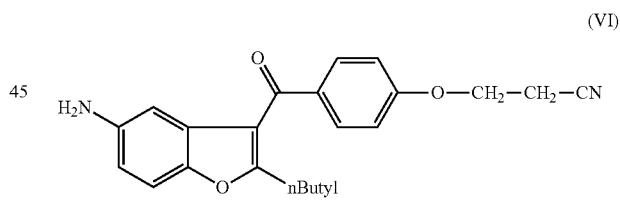

(VI)

the above compound of formula (VII) is hydrogenated.

The reaction is carried out among usual hydrogenation conditions. For example, the hydrogenation process is carried out in a solvent in the presence, of catalyst, e.g. Pd or Pt catalyst, typically Pd/C. Typically the solvent is selected from the group of $C_{1-4}$ alcohols, ethyl acetate and cyclohexane, typically the solvent is methanol or ethanol.

H) For the preparation of compound of formula (IV)

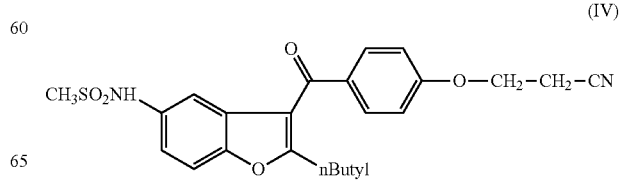

(IV)

the above compound of formula (VI) is mesylated.

Typically the reaction is carried out in an inert solvent, typically in the presence of an acid binding agent. In a specific embodiment the solvent is selected from the group of dichloromethane, dichloroethane and chlorobenzene. Typically the acid binding agent is a tertiary nitrogen base, for example pyridine or triethylamine.

In the process a mesylating reagent should be applied. It can be any reagent which can be used for inserting a $CH_3SO_2$— group into the free amino group of compound of formula (VI). It is practical to use methanesulfonic anhydride or a methanesulfonyl halogenide, e.g. methanesulfonyl chloride.

I) For the preparation of compound of formula (II)

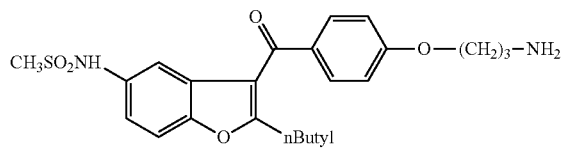

(II)

the above compound of formula (IV) is hydrogenated.

The reaction is carried out among usual hydrogenation conditions. For example the hydrogenation process is carried out in a solvent in the presence of catalyst, e.g. Ni catalyst, which is typically Raney-Ni. Typically the solvent is selected from the group of $C_{1-4}$ alcohols, ethyl acetate and cyclohexane, e.g. the solvent is methanol or ethanol.

I') However, compound of formula (II) can be prepared from another starting material, namely a compound of formula (V) [see in above point E)]

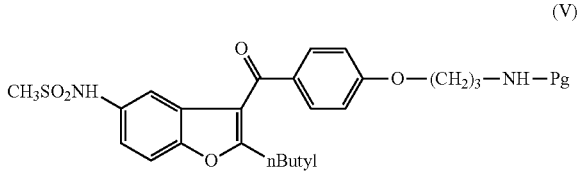

(V)

is deprotected by any known method, where Pg amino protecting group.

In formula (V) Pg is an amino protecting group, typically an A-CO— group, where A is alkyl, alkoxy, aryl or aryloxy group, e.g. it is ethoxycarbonyl.

The Pg protective group is removed according to known methods, e.g. by acidic or alkaline hydrolysis (see e.g. the following book: Philip J. Kocienski, Protecting Groups, 2005).

J) Finally, for the preparation of dronedarone (I) and pharmaceutically acceptable salts thereof

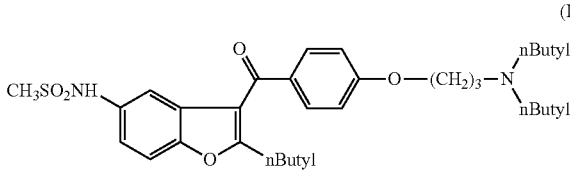

(I)

a compound of formula (II) is reacted in the presence of a reductive agent

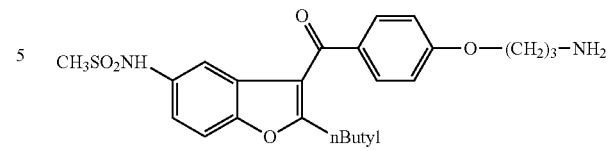

(II)

a) with butyraldehyde of formula (III) and/or

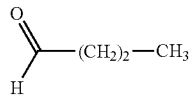

(III)

b) with butanoic acid.

Typically the above process is carried out in solvents, e.g. in a solvent selected from the group of halogenated alkanes, ethers and nitriles. The halogenated alkane is e.g. dichloromethane or 1-2-dichloroethane, the ether is e.g. tetrahydrofurane, and the nitrile is e.g. acetonitrile.

The reaction can be carried out at a temperature between 5° C. and 80° C. When triacetoxyborohydride is applied, then the temperature is typically 10-30° C. When sodium borohydride and butanoic aside are applied, then the temperature is typically 30-60° C.

Typically triacetoxyborohydride is applied as reductive agent when butyraldehyde is used as butylating reagent. Typically sodium borohydride is applied as reductive agent when butanoic acid is used as butylating reagent. In this reaction butyraldehyde of formula (III) also can be present in the reaction medium (surprisingly, in this case a better yield can be achieved).

The amount of triacetoxyborohydride or sodium borohydride is typically 1 to 5 equivalents. The amount of butyraldehyde is 2 to 4 equivalents when using triacetoxyborohydride and 0 to 2 equivalents when using sodium borohydride, where the equivalents are calculated for compound of formula (II).

As used herein, the term alkyl includes straight or branched aliphatic hydrocarbon chains of 1 to 6 carbon atoms, e.g., methyl, ethyl, isopropyl and t-butyl.

The temperature applied in the reaction is typically between 0° C. and the boiling point of the solvent (which can be the mixture of the mentioned solvents, too), e.g. between 60-120° C. Typically the atmospheric pressure is applied during the reaction.

The applicable acid for the preparation of pharmaceutically acceptable salts can be any inorganic or organic acid which forms an acid addition salt with the compound of general formula (I). Exemplary acids which can form an acid addition salt are as follows: acetic acid, adipic acid, alginic acid, ascorbic acid, aspartic acid, benzoic acid, benzenesulfonic acid, methansulfonic acid, ethansulfonic acid, boric acid, butyric acid, citric acid, fumaric acid, hydrogen chloride, hydrogen bromide, hydrogen iodide, 2-hydroxyethanesulfonic acid, maleic acid, oxalic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compound of general formula (I) (see the "left side" of the molecules) a salt formation can be carried out (on the amide part of it) by a strong base, e.g. an alkaline hydroxide, typically by sodium hydroxide. However, these salts have less practical importance, but they are within the scope of salts which can be prepared by the claimed process. It means that the phrase "salts" embraces both the acid addition salts and the salts formed by bases (basic salts) in case of compounds of general formula (I).

Other objects of the invention are the novel intermediary compounds applied in the processes, namely the following compounds:

The compound of formula (II) and salts thereof (II)

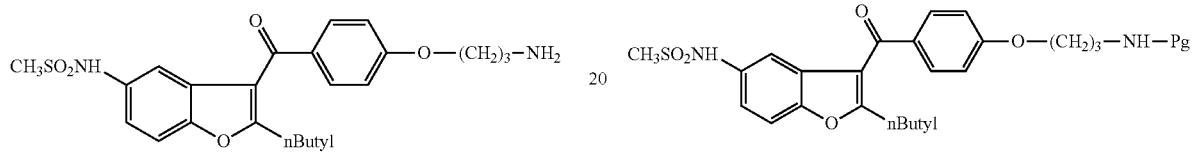

The compound of formula (IV) and salts thereof (IV)

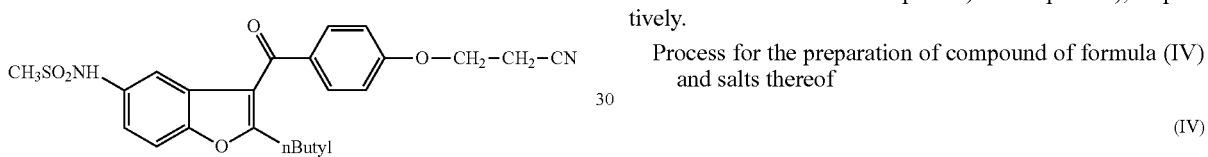

The compounds of formula (V) and salts thereof (V)

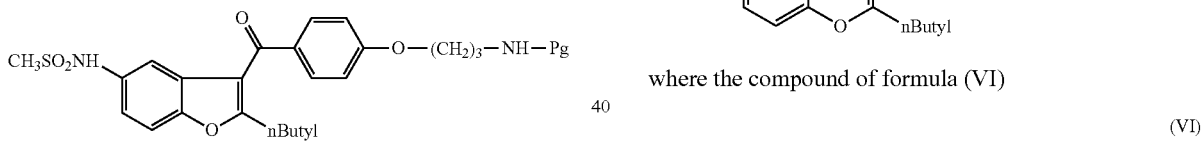

where Pg is an amino protecting group, typically an A-CO— group, where A is alkyl, alkoxy, aryl or aryloxy group, e.g. it is ethoxycarbonyl.

The compound of formula (VI) or salts thereof (VI)

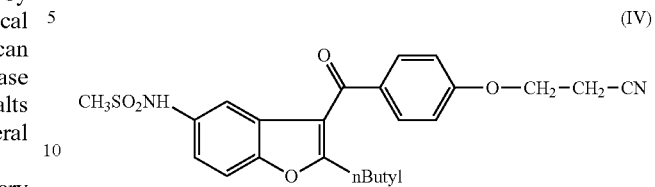

The compound of formula (VII)

(VII)

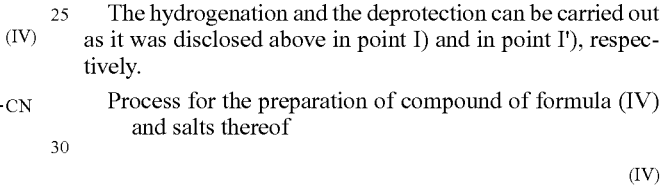

Other objects of the invention are the processes for the preparation of the novel intermediary compounds, namely the following ones:

Process for preparation of compound of formula (II) and salts thereof where a) the compound of formula (IV)

(IV)

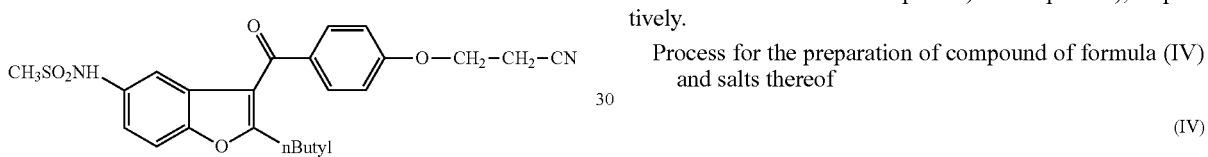

is hydrogenated or b) a compound of formula (V)

(V)

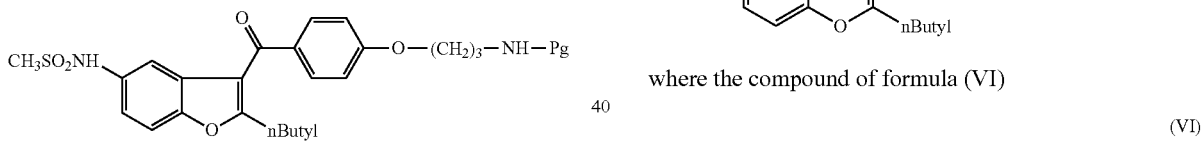

is deprotected where Pg is an amino protecting group.

The hydrogenation and the deprotection can be carried out as it was disclosed above in point I) and in point I'), respectively.

Process for the preparation of compound of formula (IV) and salts thereof (IV)

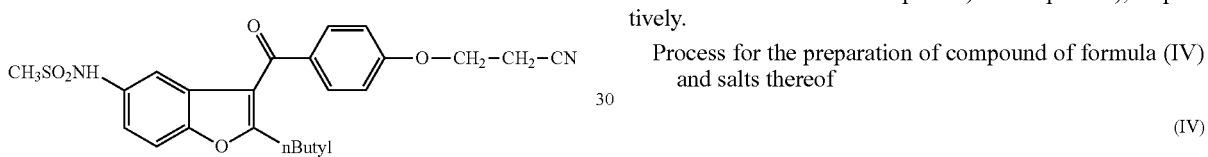

where the compound of formula (VI)

(VI)

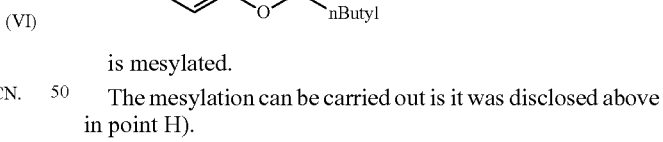

is mesylated.

The mesylation can be carried out is it was disclosed above in point H).

Process for preparation of compounds of formula (V) and salts thereof (V)

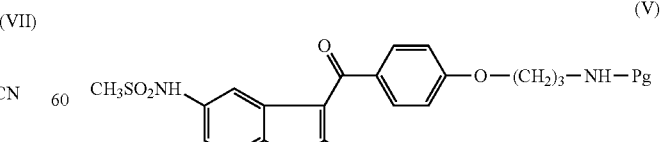

where Pg is an acyl group deriving from an A-CO— group, where A is alkyl, alkoxy, aryl or aryloxy group, e.g. it is ethoxycarbonyl, where the compound of formula (X)

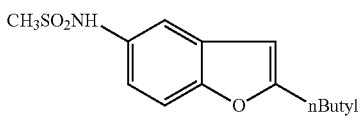

is reacted with compound of formula (XI)

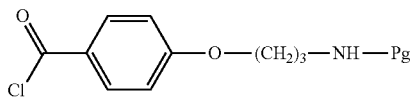

under Friedel-Crafts reaction conditions, where Pg is amino protecting group, typically an A-CO— group, where A is alkyl, alkoxy, aryl or aryloxy group, e.g. it is ethoxycarbonyl.

The reaction can be carried out is it was disclosed above in point E).

Process for the preparation of compound of formula (VI) and salts thereof

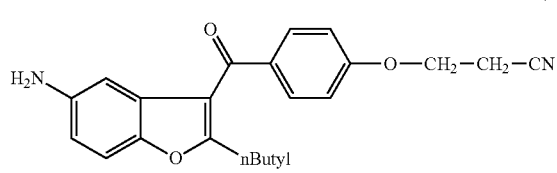

where the compound of formula (VII)

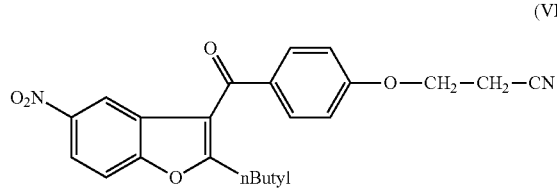

is hydrogenated.

The hydrogenation can be carried out is it was disclosed above in point G).

Process for the preparation of compound of formula (VII)

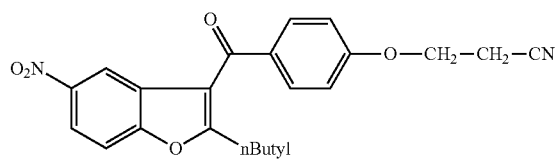

where the compound of formula (VIII)

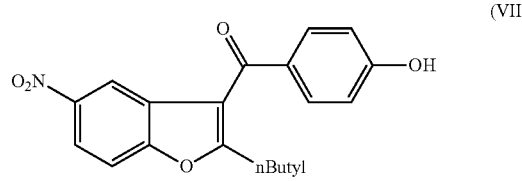

is reacted with acrylonitrile of formula ($CH_2=CH-CN$) (IX).

The reaction can be carried out is it was disclosed above in point F).

In the processes for the preparation of the intermediary compounds the product is isolated as a base typically (if the compound has a free amino or an alkylated amino group). If desired, the isolated base can be converted into a salt (acid addition salt) thereof, which is typically a pharmaceutically acceptable salt [the possible acids are mentioned in point F)]. Theoretically the acid addition salt can be prepared directly if the relating acid is in the final reaction mixture from which the solid product is made (however, this way is not applied in case of these compounds where the base type form has practical importance).

Here it is mentioned that some of the above intermediary compounds have a mesylate group (see the "left side" of the molecules) where a salt formation can be carried out (on the amide part of it) by a strong base, e.g. an alkaline hydroxide, typically by sodium hydroxide. However, these salts have less practical importance, but they are within the scope of salts which can be prepared by the claimed process, i.e. the phrase "salts" embraces the salts formed by bases (basic salts) in such cases (where the molecule has a mesylate group).

In the above reactions the temperature is chosen according to the general practice of a person skilled in organic chemistry. Typically the temperature is between 10° C. and the boiling point of the applied solvent (which can be the mixture of the mentioned solvents in a specific embodiment). Applicable temperature values can be found in the examples.

All the above reactions are carried out under atmospheric pressure with the exception of the hydrogenation steps where higher pressure also can be applied, typically up to 20 bar, e.g. 5 to 10 bar.

As used herein, the term alkyl includes straight or branched aliphatic hydrocarbon chains of 1 to 6 carbon atoms, e.g., methyl, ethyl, isopropyl and t-butyl.

As used herein, the term "alkoxy" includes alkyl-O— groups. Non-limiting examples of suitable alkoxy groups include methoxy, ethoxy, n-propoxy, isopropoxy and n-butoxy.

As used herein, the term "aryl" includes aromatic monocyclic or multicyclic ring systems comprising 6 to about 14 carbon atoms, preferably 6 to about 10 carbon atoms. Non-limiting examples of suitable aryl groups include phenyl and naphthyl.

As used herein, the term "aryloxy" includes aryl-O— groups.

As used herein, the term "halogen" includes fluoro, chloro, bromo and iodo atoms.

EXAMPLES

Example 1

N-[2-butyl-3-{4-[(3-dibutylamino)propoxy]benzoyl}-1-benzofuran-5-yl]methanesulfonamide (I)

1 g of N-[2-butyl-3-{4-[(3-amino)propoxy]benzoyl}-1-benzofuran-5-yl]-methansulfonamide is dissolved in 30 ml of dichloromethane. 0.5 g of butyraldehyde and 1.8 g of triacetoxyborohydride is added, and the reaction mixture is stirred at 20° C. for 12 hours. The reaction mixture is evaporated and the residue is dissolved in isopropyl acetate. The solution is washed with 20 ml of water, with 10 ml of 5% NaHCO$_3$ solution and with 10 ml of water. The solvent is evaporated.

Yield: 1.21 g (94.5%).

This product is purified by forming its oxalate salt as follows: to the residue 6 ml of methylethyl ketone is added and the mixture heated to 70° C. To this solution 0.26 g of oxalic acid dissolved in 2.5 ml of methylethyl ketone is added at 70°

C. After cooling to 20° C. in 6 hours the mixture is stirred at 10° C. for 1 hour and filtered. To the obtained oxalate salt 4 ml of water and 6 ml of dichloromethane and 0.70 g of potassium carbonate are added. After stirring for 30 minutes the separated potassium oxalate is filtered and washed with 3 ml of dichloromethane and the solvent is evaporated.

Mass of purified product 1.08 g (89%).
Purity of product: 99.7% (HPLC).
1H NMR (DMSO): 0.8-0.9 ppm (m, 9H); 1.2-1.5 ppm (m, 10H); 1.67 ppm (5', 2H); 1.87 ppm (5', 2H); 2.38 ppm (t, J=7.2 Hz, 4H); 2.57 ppm (m, 2H); 2.88 ppm (t, J=7.5 Hz, 2H); 2.91 ppm (s, 3H); 9.51 ppm (t, J=6.2 Hz, 2H); 7.09 ppm (d, J=8.8 Hz, 2H); 7.24 ppm (dd, J=8.9, 2.2 Hz, 1H); 7.38 ppm (d, J=2.1 Hz, 1H); 7.65 ppm (d, J=8.8 Hz, 1H); 7.81 ppm (d, J=8.8 Hz, 2H)

Example 2

N-[2-butyl-3-{4-[(3-dibutylamino)propoxy]benzoyl}-1-benzofuran-5-yl]methanesulfonamide (I)

1 g of N-[2-butyl-3-{4-[(3-amino)propoxy]benzoyl}-1-benzofuran-5-yl]methanesulfonamide is dissolved in 12 ml of butanoic acid. 0.2 g of butyraldehyde and 0.26 g of sodium borohydride are added. The mixture is stirred at 55° C. for 8 hours. Cooled down to 0° C. and 20 ml of water is added. The mixture is made strongly basic with solid potassium hydroxide and extracted with 2×20 ml of dichloromethane. The solution is washed with 25 ml of water, with 15 ml of 5% NaHCO$_3$ and with 10 ml of water, and evaporated.

Yield: 1.10 g (85.9%)
The product is purified through its oxalate salt according to Example 1 (87%).
Purity of product: 99.6% (HPLC). The product is identical with the compound prepared in example 1.

Example 3

N-[2-butyl-3-{4-[(3-dibutylamino)propoxy]benzoyl}-1-benzofuran-5-yl]methanesulfonamide (I)

1 g of N-[2-butyl-3-{4-[(3-amino)propoxy]benzoyl}-1-benzofuran-5-yl]methanesulfonamide is dissolved in 12 ml of butanoic acid and 0.39 g of sodium borohydride are added. The mixture is stirred at 55° C. for 8 hours. Cooled down to 0° C. and 20 ml of water is added. The mixture is made, strongly basic with solid potassium hydroxide and extracted with 2×20 ml of dichloromethane. The solution is washed with 25 ml of water, with 15 ml of 5% NaHCO$_3$ and with 10 ml of water, and evaporated.

Yield: 0.88 g (69%)
The product is purified through its oxalate salt according to Example 1 (81%).
Purity of product: 99.4% (HPLC). The product is identical with the compound prepared in example 1.

Example 4

N-[2-butyl-3-{4-[(3-dibutylamino)propoxy]benzoyl}-1-benzofuran-5-yl]methanesulfonamide (I)

The process is performed according to example 1 with the difference that instead of dichloromethane 1,2-dichloroethane is used.

The product is purified through its oxalate salt according to Example 1. Yield of purified product: 1.1 g (86%). Purity: 99.7% (HPLC).

Example 5

N-[2-butyl-3-{4-[(3-dibutylamino)propoxy]benzoyl}-1-benzofuran-5-yl]methanesulfonamide (I)

The process is performed according to example 2 with the difference, that to the reaction 15 ml of tetrahydrofurane is added.

The product is purified through its oxalate salt according to Example 1. Yield of purified product: 1.05 g (85%). Purity: 97.6% (HPLC).

Example 6

N-[2-butyl-3-{4-[(3-amino)propoxy]benzoyl}-1-benzofuran-5-yl]methanesulfonamide (II)

3.0 g of N-[2-butyl-3-{4-[2-cyanoethoxy]benzoyl}-1-benzofuran-5-yl]methanesulfonamide is dissolved in 300 ml of methanol and 5 g of Raney-Ni catalyst is added. The mixture is stirred at 25° C. at 10 bar H$_2$ pressure for 24 hours. The catalyst is filtered and the solvent is evaporated.

Yield: 2.94 g (98%). Purity: 75% (HPLC).
1H NMR (DMSO): 7.77 ppm (d, J=8.7 Hz, 2H); 7.59 ppm (d, J=8.70 Hz, 1H); 7.23 ppm (d, J=2.06 Hz, 1H); 7.18 ppm (dd, J=8.81, 2.17 Hz, 1H); 7.07 ppm (d, J=8.7 Hz, 2H); 4.14 ppm (t, J=6.41 Hz, 2H); 2.85 ppm (s, 3H); 2.80 ppm (t, J=7.10 Hz, 2H); 2.71 ppm (t, J=6.75 Hz, 2H); 1.82 ppm (quin, J=6.52 Hz, 2H); 1.65 ppm (quin, J=7.30 Hz, 2H); 1.24 ppm (5xt, J=7.32 Hz, 2H); 0.80 ppm (t, J=7.32 Hz, 3H)
Molecular mass: [M+H]$^+_{measured}$=445.1781 Da; [M+H]$^+_{calc.}$=445.1797 Da Example 7

N-[2-butyl-3-{4-[2-cyanoethoxy]benzoyl}-1-benzofuran-5-yl]methanesulfonamide (IV)

4.0 g of (5-amino-2-butyl-benzofur-3-yl)-[4-(2-cyanoethoxy)phenyl]methanon is dissolved in 40 ml of dichloromethane. The mixture is warmed to 30-35° C. and 1.05 g of pyridine is added at this temperature in 5 minutes. At this temperature 1.5 g of methanesulfochloride is added in 5 minutes and the mixture is stirred at 30-35° C. for 3 hours. The mixture is cooled to 20° C. and washed with 2×15 ml of water, 2×15 ml of 5% NaHCO$_3$ and 1×15 ml of water. The phases are separated and the dichloromethane evaporated.

Yield: 4.81 g (100%).
Purity: 94.8% (HPLC). Mp.: 120.9-121.7° C.
1H NMR (DMSO): 9.6 ppm (s, 1H) 7.79 ppm (d, J=8.93 Hz, 2H) 7.62 ppm (d, J=8.93 Hz, 1H) 7.27 ppm (d, J=2.06 Hz, 1H) 7.21 ppm (dd, J=8.70, 2.06 Hz, 1H) 7.13 ppm (d, J=8.93 Hz, 2H) 4.31 ppm (t, J=5.84 Hz, 2H) 3.07 ppm (t, J=5.84 Hz, 2H) 2.88 ppm (s, 3H) 2.80 ppm (t, J=7.44 Hz, 2H) 1.65 ppm (quin, J=7.44 Hz, 2H) 1.24 ppm (sxt, J=7.37 Hz, 2H) 0.80 ppm (t, J=7.44 Hz 3H)

Example 8

5-amino-2-butyl-benzofur-3-yl)-[4-(2-cyanoethoxy)phenyl]methanon (VI 1 g of (5-nitro-2-butyl-benzofur-3-yl)-[4-(2-cyanoethoxy)phenyl]methanon is dissolved in 15 ml of methanol and 0.1 g of 10% wet Pd/C catalyst is added and the reaction mixture is heated to 50° C. at a stirring speed of 800 round/min (rpm). Hydrogen pressure of 5 bar is set to the reactor and the mixture is stirred at this temperature for 2 hours. After cooling to room temperature the catalyst is filtered out and the solvent is evaporated.

Yield: 0.92 g (100%). Purity (HPLC): 97.3%.

1H NMR (DMSO): 7.76 ppm (d, J=8.93 Hz, 2H); 7.26 ppm (d, J=8.70 Hz, 1H); 7.12 ppm (d, J=8.70 Hz, 2H); 6.57 ppm (dd, J=8.70, 2.29 Hz, 1H); 6.49 ppm (d, J=2.29 Hz, 1H); 4.30 ppm (t, J=5.84 Hz, 2H); 3.06 ppm (t, J=5.84 Hz, 2H); 2.73 ppm (t, J=7.55 Hz, 2H); 1.62 ppm (quin, J=7.50 Hz, 2H); 1.23 ppm (sxt, J=7.28 Hz, 3H); 0.80 ppm (t, J=7.32 Hz, 4H)

Molecular mass: $[M+H]^+_{measured}$=363.1711 Da; $[M+H]^+_{calc.}$=363.1709 Da

Example 9

5-nitro-2-butyl-benzofur-3-yl)-[4-(2-cyanoethoxy)phenyl]methanon (VII 27.8 g of (2-butyl-5-nitro-1-benzofur-3-yl)-(4-hydroxyphenyl)methanon, 43.5 g of acrylonitrile and 18 g Triton B (benzyltrimethylammonium hydroxide) are added and heated under stirring to 80-85° C. and stirred at this temperature for 48 hours. After cooling to room temperature the reaction mixture is evaporated and the acrylonitrile is recovered for the next trial. To the residue 150 ml of dichloromethane is added and washed with 3×80 ml of 5% sodium hydroxide. From the sodium hydroxide solution 16.2 g of starting (2-butyl-5-nitro-1-benzofur-3-yl)-(4-hydroxyphenyl)methanon is recovered. The dichloromethane solution is evaporated.

Yield: 12.07 g (94.2% for the consumed starting material). Purity: 97.6% (HPLC). Mp.: 108.6-108.9° C.

1H NMR (DMSO): 0.80 ppm (t, J=7.44 Hz, 3H); 1.24 ppm (sxt, J=7.37 Hz, 2H); 1.68 ppm (quin, J=7.50 Hz, 2H); 2.84 ppm (t, J=7.55 Hz, 2H); 3.07 ppm (t, J=5.95 Hz, 2H); 4.33 ppm (t, J=5.95 Hz, 2H); 7.15 ppm (d, J=8.70 Hz, 2H); 7.84 ppm (d, J=8.70 Hz, 2H); 7.92 ppm (d, 9.84 Hz, 1H); 8.22-8.28 ppm (m, 2H)

Example 10

N-[2-butyl-3-{4-[(3-amino)propoxy]benzoyl}-1-benzofuran-5-yl]methanesulfonamide (II)

4.0 g of N-[2-butyl-3-{4-[(3-ethoxycarbonylamino)propoxy]benzoyl}-1-benzofuran-5-yl]-methanesulfonamide is added to 30 ml of methanol and 0.62 g of sodium hydroxide is added. The reaction mixture is boiled for 3 hours and the solvent is evaporated. To the solid material 20 ml of water is added and the pH of the solution is set to pH=6. The separated oil is extracted with 20 ml of dichloromethane. The dichloromethane is evaporated. The residual material is identical with compound prepared in example 5.

Yield: 2.8 g (82%.) Purity: 79% (HPLC).

Example 11

N-[2-butyl-3-{4-[(3-ethoxycarbonylamino)propoxy]benzoyl}1-benzofuran-5-yl]methanesulfonamide (V)

1.6 g of N-(2-butyl-1-benzofuran-5-yl)methanesulfonamide and 15 ml of dichloromethane are stirred at room temperature for 5 minutes. To this suspension 2.4 g of 4-[(3-carbethoxyamino)-propoxy]benzoylchloride is added slowly. The mixture is cooled down to 5° C. and 1.21 g of Fe(III)chloride is added in 4 portions in 20 minutes at a temperature of 5-10° C. The mixture is stirred for additional 3 hours at 20° C. The mixture is heated to 4.0-45° C. and 27 ml of water is added in 20 minutes. The reaction mixture is stirred at this temperature for 30 minutes. The phases are separated and the organic phase is washed with 1×8 ml of water, 2×8 ml of 5% NaHCO$_3$ and with 2×8 ml of water. The solvent is evaporated. The residual material is purified with chromatography on silica gel, using ethyl acetate/hexane mixture (1:3) as eluent.

Yield of purified product: 1.45 g (72.1%).
Purity (HPLC): 91.2%. Mp.: 155.7-156.9° C.

1H NMR (DMSO): 9.57 ppm (s, 1H); 7.77 ppm (d, J=8.7 Hz, 2H); 7.61 ppm (d, J=8.8 Hz, 1H); 7.27 ppm (d, J=1.6 Hz, 1H); 7.20 ppm (dd, J=8.8, 2.1 Hz, 1H); 7.17 ppm (t, 5.0 Hz, 1H); 7.06 ppm (d, J=8.6 Hz, 2H); 4.09 ppm (t, J=6.2 Hz, 2H); 3.97 ppm (q, J=7.1 Hz, 2H); 3.15 ppm (q, J=6.2 Hz, 2H); 2.88 ppm (s, 3H); 2.80 ppm (t, J=7.4 Hz, 2H); 1.88 ppm (5', H=6.4 Hz, 2H); 1.65 ppm (5', J=7.4 Hz, 2H); 1.23 ppm (6', J=7.4 Hz, 2H); 1.14 ppm (t, J=7.0 Hz, 3H); 0.80 ppm (t, J=7.3 Hz, 3H)

Example 12

4-[(3-carbethoxyamino)propoxy]benzoic acid (XII)

0.4 g of sodium hydroxide and 1.06 g of sodium carbonate are dissolved in 8 ml of water. 1.15 g of 4-[3-aminopropoxy]benzoic acid is added to this solution under stirring. The mixture is cooled to 10° C. and stirred at this temperature for 1 hours. 1.09 g of ethoxycarbonyl chloride is added in 20 minutes and the mixture is stirred at 25° C. for 3 hours. The mixture is extracted with 25 ml of dichloromethane and the phases are separated. The pH of the aqueous solution is set to pH=1 with diluted hydrochlorid acid and the separated white material is stirred at 10° C. for 1 hours and filtered, washed with 3×10 ml of water and dried under reduced pressure at 70° C.

Yield: 1.07 g (81%.) Purity (HPLC): 92.8%. Mp.: 147.9-149.1° C.

1H NMR (DMSO): 12.6 ppm (w, 1H); 7.87 ppm (d, 8.8 Hz, 2H); 7.16 ppm (t, J=5.6 Hz, 1H); 6.99 ppm (d, J=8.8 Hz, 2H); 4.05 ppm (t, J=6.2 Hz, 2H); 3.96 ppm (q, J=7.1 Hz, 2H); 3.13 ppm (q, J=6.1 Hz, 2H); 1.86 ppm (5', J=6.5 Hz, 2H); 1.14 ppm (t, J=7.0 Hz, 3H)

Example 13

4-(3-aminopropoxy)benzoic acid HCl salt (XIII)

24.5 g of methyl[4-3(aminopropoxy)benzoate] is added to an aqueous solution prepared from 8.4 g of sodium hydroxide and 33.6 ml of water. 56 ml of methanol is added under stirring and the mixture is boiled for 6 hours. The solvent is evaporated. To the solid residue 150 ml of water is added and the solution is extracted with 20 ml of dichloromethane. The pH of the aqueous solution is set to pH=1 with diluted hydrochloric acid. The separated material is washed with 3×100 ml of water and dried under reduced pressure at 70° C.

Yield: 23 g (85.8%.) Purity: 87% (HPLC). Mp.: 270.0-279.8° C.

Example 14

Methyl[4-(3-aminopropoxy)benzoate] (XIV)

2.1 g of methyl(2-cyanoethoxy)benzoate (prepared according to the method in JP Appl. No 19660803) is dissolved in 30 ml of methanol. 0.5 g of Raney-Ni is added and the mixture is hydrogenated at 50° C. under 10 bar of hydrogen pressure for 4 hours. The catalyst is filtered and the solvent evaporated to obtain the product as an oil [Helv. Chim. Acta Vol. 66. Fasc. 2 (1983) No. 42].

Yield: 2.1 g (100%.) Purity: 84% (HPLC).

The invention claimed is:

1. A process for preparing dronedarone of formula (I) and pharmaceutically acceptable salts thereof

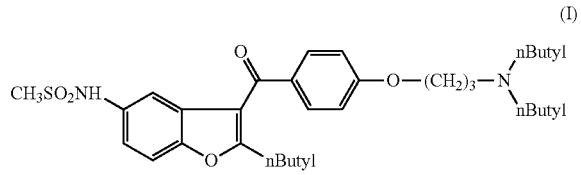
(I)

comprising reacting a compound of formula (II)

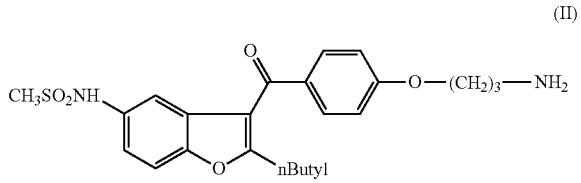
(II)

in the presence of a reductive agent with
a) butyraldehyde of formula (III) and/or

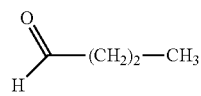
(III)

b) butanoic acid,
and isolating the obtained product and, optionally, converting it into a pharmaceutically acceptable salt thereof.

2. The process according to claim, 1 wherein triacetoxyborohydride is applied as reductive agent when butyraldehyde is used as butylating reagent and sodium borohydride is applied as reductive agent when butanoic acid is used as butylating reagent.

3. The process according to claim, 2 wherein the amount of triacetoxyborohydride or sodium borohydride is 1 to 5 equivalents, the amount of butyraldehyde is 2 to 4 equivalents when using triacetoxyborohydride and 0 to 2 equivalents when using sodium borohydride, where the equivalents are calculated for compounds of formula (II).

4. A process of preparing the compound of formula (II) in claim 1, comprising
a) hydrogenating a compound of formula (IV)

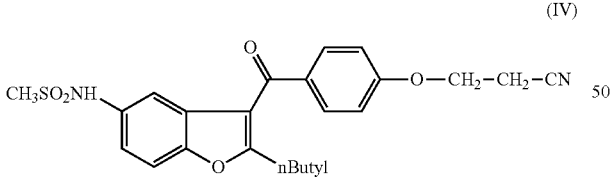
(IV)

Or
b) deprotecting a compound of formula (V)

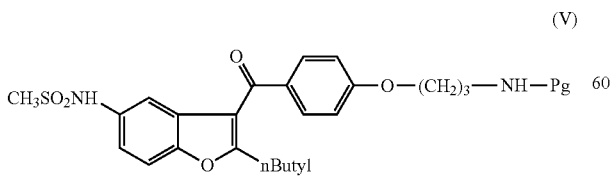
(V)

where Pg is an amino protecting group,
and isolating the obtained product and, optionally, converting it into a salt thereof.

5. A compound of formula (IV) and salts thereof

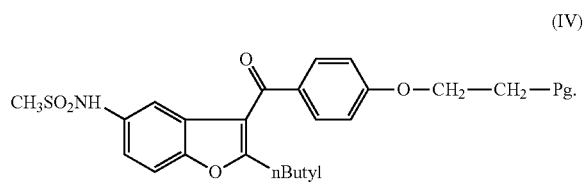
(IV)

6. A process for preparing the compound of claim 5 and salts thereof
comprising mesylating a compound of formula (VI)

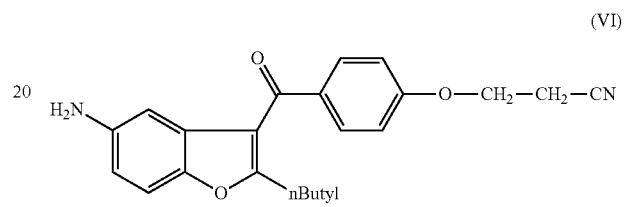
(VI)

and isolating the obtained product and, optionally, converting it into a salt thereof.

7. A compound of formula (V) and salts thereof

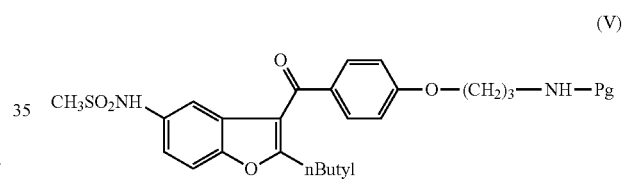
(V)

where Pg is an amino protecting group.

8. The compound according to claim 7, wherein the Pg amino protecting group is an A-CO— group, where A is alkyl, alkoxy, aryl or aryloxy group.

9. A process for preparing the compound claim 7 and salts thereof
comprising reacting a compound of formula (X)

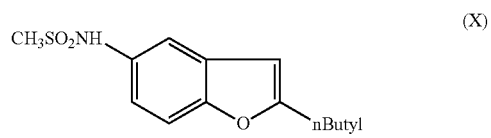
(X)

with a compound of formula (XI)

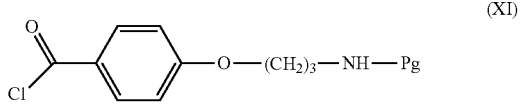
(XI)

under Friedel-Crafts reaction conditions, where Pg is amino protecting group, and isolating the obtained product and, optionally, converting it into a salt thereof.

10. A compound of formula (VI) and salts thereof

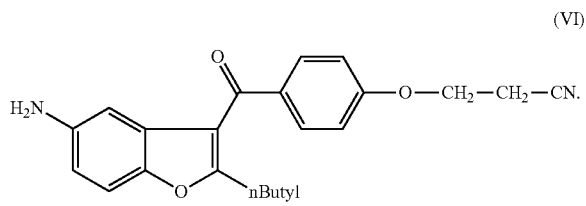
(VI)

11. A process for preparing the compound of claim 10 and salts thereof
comprising hydrogenating a compound of formula (VII)

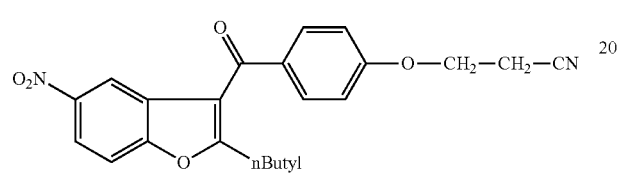
(VII)

and isolating the obtained product and, optionally, converting it into salt thereof.

12. A compound of formula (VII)

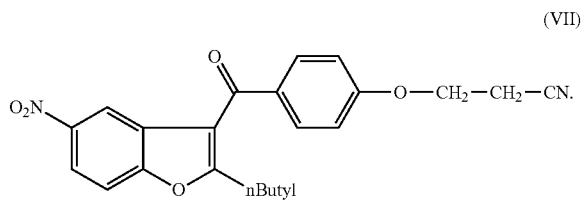
(VII)

13. A process for preparing the compound of claim 12 comprising reacting a compound of formula (VIII)

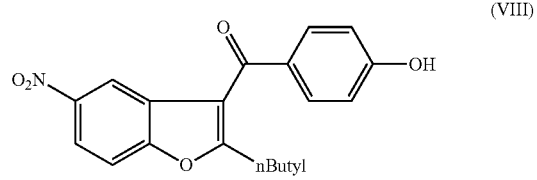
(VIII)

with acrylonitrile of formula $CH_2=CH-CN$ (IX), and isolating the obtained product.

* * * * *

UNITED STATES PATENT AND TRADEMARK OFFICE
CERTIFICATE OF CORRECTION

PATENT NO. : 9,024,046 B2
APPLICATION NO. : 14/007170
DATED : May 5, 2015
INVENTOR(S) : Antal Friesz et al.

It is certified that error appears in the above-identified patent and that said Letters Patent is hereby corrected as shown below:

Title Page:

In the Abstract, item (57), in line 2, replace "drohedarone" with --dronedarone--;

In the Abstract, item (57), in line 8, replace "hovel" with --novel--.

In the Claims:

At column 19, claim 2, line 32, replace "claim, 1" with --claim 1,--;

At column 19, claim 3, line 37, replace "claim, 2" with --claim 2,--;

At column 20, claim 5, formula (IV), starting on line 3, replace

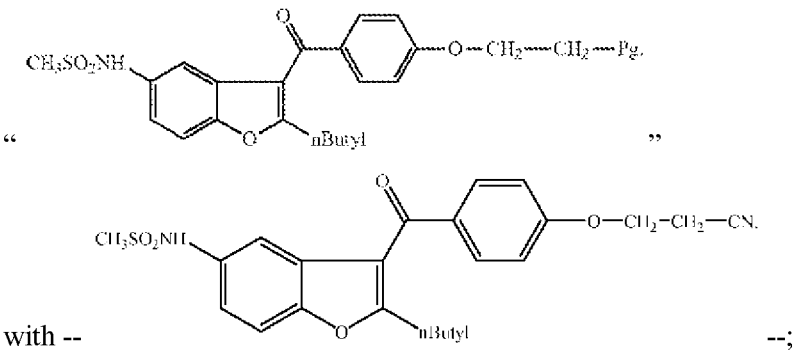

At column 20, claim 9, line 65, replace "Pg is amino" with --Pg is an amino--; and At column 21, claim 11, line 28, replace "into salt thereof." with --into a salt thereof.--.

Signed and Sealed this
Eighth Day of December, 2015

Michelle K. Lee
*Director of the United States Patent and Trademark Office*